(12) United States Patent
Blodgett et al.

(10) Patent No.: US 8,120,758 B2
(45) Date of Patent: Feb. 21, 2012

(54) FAST UV-VIS-NIR ABSORPTION SPECTROMETER SYSTEM AND METHOD

(75) Inventors: Troy Blodgett, Flagstaff, AZ (US); Matt Hall, West Chester, PA (US); Thomas Scott Hemphill, Lexington, MA (US); Wuyi Wang, Edison, NJ (US)

(73) Assignee: Gemological Institute of America, Inc., Carlsbad, CA (US)

( * ) Notice: Subject to any disclaimer, the term of this patent is extended or adjusted under 35 U.S.C. 154(b) by 328 days.

(21) Appl. No.: 12/380,425

(22) Filed: Feb. 27, 2009

(65) Prior Publication Data

US 2010/0220310 A1    Sep. 2, 2010

(51) Int. Cl.
  *G01N 21/87* (2006.01)
(52) U.S. Cl. .......................................... 356/30
(58) Field of Classification Search ...................... 356/30
  See application file for complete search history.

(56) References Cited

U.S. PATENT DOCUMENTS 5,835,200 A * 11/1998 Smith et al. ..................... 356/30
6,377,340 B1 * 4/2002 Anthony et al. ................. 356/30

* cited by examiner

*Primary Examiner* — F. L. Evans
(74) *Attorney, Agent, or Firm* — DLA Piper LLP (US)

(57) ABSTRACT

A method and system for evaluating a colored gem stone which has been cooled to below a designated temperature are provided. The system includes a cooling unit configured to support and cool a gem stone to below a desired temperature, an electromagnetic radiation source, a spectrometer, an integrating sphere, and a processing unit. The method includes receiving a spectral response of the colored gem stone and sampling a noise component within a range of wavelengths in the spectral response so as to make a baseline determination. The method further includes ascertaining a presence of at least one designated peak within the range of wavelengths as a function of the baseline determination, and evaluating the presence of each of the at least one designated peaks so as to provide an indication of whether the colored gem stone requires further evaluation.

27 Claims, 4 Drawing Sheets

FAST UV-VIS-NIR ABSORPTION SPECTROMETER SYSTEM AND METHOD

TECHNICAL FIELD

The present invention is directed generally to spectral analysis of gems, and more particularly to a system and method for rapidly obtaining and analyzing the spectral response of a gem to electromagnetic radiation to screen gems that have been potentially color enhanced through radiation, high temperature, high pressure, coatings, or a combination of these treatments.

BACKGROUND OF THE TECHNOLOGY

Evaluation of gems, such as colored gems, often involves analysis of the spectral response of the gems to a variety of wavelengths of electromagnetic radiation, for example, in the UV, visible, and Near Infrared range, to search for indicators of color origin. Typical spectral responses can appear as a complex spectrum of peaks, slopes and plateaus over the wavelength range of interest.

For example, as described in the article, entitled "Insider Gemologist: Tests to Distinguish Natural from Treated Yellow Diamonds," Feb. 23, 2001, Vol. 3, Issue 4, Gemological Institute of America, distinguishing natural-color yellow diamonds from treated ones may involve the use of a spectroscope to view the absorption spectra of a diamond for absorption bands known as the "Cape" lines, and for other lines. These Cape lines occur in most natural-color yellow diamonds at 478 nm, 465 nm, 452 nm. Other lines of interest may include a strong line at 415 nm. On the other hand, while treated diamonds may show one or more of these "Cape" lines, they also show a pair of strong absorption lines at 503 nm and 496 nm. In some cases an absorption band known as the "heat line" at 595 nm may be seen. The "heat line" is produced during an annealing step which transforms an irradiated diamond from a blue or green color to yellow. At the time of the article, the most common treatment for producing yellow color in diamonds was a combination of irradiation (either in a nuclear reactor or by use of an electron beam) and annealing, also known as controlled heating.

Conventional techniques for determining whether a gem stone has been subjected to color-altering treatment have involved the use of time consuming manual visual analysis of absorption spectra, or further evaluation of the results of generic spectral analysis algorithms, as well as the use of cumbersome cryostats, or other cooling techniques having their own disadvantages. As a result, such conventional analysis techniques suffer from significant per-stone analysis times. Further, the noise levels present in previous arrangements for acquiring spectral responses have limited the size of peaks that could be resolved in the acquired spectral responses. As a result of these and other limitations, conventional approaches typically rely on personnel who are highly skilled in spectral interpretation, have been prone to variations in consistency in applying analysis criteria to the acquired spectral responses, and have required substantial time to perform an analysis of each gem stone.

It is therefore desirable to have a method and system that is capable of the above spectral analysis in less time, with greater consistency, and with higher resolution than prior techniques.

SUMMARY OF THE INVENTION

This invention addresses the aforementioned problems of previous method and systems for obtaining and analyzing the spectral response of a gem.

In an embodiment of the invention, a method is provided for evaluating a gem stone which has been cooled to below a designated temperature. The method includes obtaining a spectral response of the colored gem stone over ranges of wavelengths of electromagnetic radiation, and evaluating the spectral response for the presence and character of a plurality of designated peaks. The method also includes generating a pass indication or a refer indication as a function of a combination of results from an evaluation of characteristics of a plurality of designated peaks. Within such embodiment, the evaluating step includes determining from the spectral response a corresponding linear peak baseline for peaks of the plurality of designated peaks, and determining for each of the plurality of designated peaks, a height of the designated peak above the corresponding linear peak baseline. The evaluating step also includes indicating that a designated peak has been found when the determined height of the designated peak above the corresponding linear peak baseline equals or exceeds a first designated threshold.

In a further embodiment of the invention, a method is again provided for evaluating a colored gem stone which has been cooled to below a designated temperature, which includes obtaining a spectral response of the colored gem stone over a range of wavelengths of electromagnetic radiation. This method further includes evaluating the spectral response with a diamond with isolated nitrogen impurity metric for the presence of an Ib characteristic, evaluating the spectral response for the presence of a Cape Ratio, and evaluating the spectral response for the presence of a plurality of designated peaks including a radiation peak and cape peaks. Within such embodiment, the method also includes generating a pass indication or a refer indication as a function of results of the Ib metric evaluation, results of the radiation and cape peaks evaluation, and results of the Cape Ratio evaluation.

In another embodiment of the invention, a system for processing spectral information from a gem stone is provided. The system includes a cooling unit configured to support and cool a gem stone to below a desired temperature, an electromagnetic radiation source, a spectrometer, an integrating sphere, and a processing unit. Within such embodiment, the integrating sphere is coupled to the electromagnetic radiation source and to the spectrometer, and positionable in the cooling unit to provide to the spectrometer responsive electromagnetic spectrum collected from a gem stone supported in the cooling unit and which has been illuminated with electromagnetic radiation from the electromagnetic radiation source. Also within such embodiment, the processing unit is configured to analyze spectral response information received from the spectrometer. The analysis performed by the processing unit includes evaluating the spectral response with an Ib metric for the presence of an Ib characteristic, evaluating the spectral response for the presence of a Cape Ratio, and evaluating the spectral response for the presence of a plurality of designated peaks including a radiation peak and cape peaks. A pass indication or a refer indication is generated by the processing unit as a function of results of the Ib metric evaluation, results of the radiation and cape peaks evaluation, and results of the Cape Ratio evaluation.

In a still further embodiment of the invention, a method for evaluating a colored gem stone which has been cooled to below a designated temperature is provided. The method includes receiving a spectral response of the colored gem stone, and sampling a noise component within a range of wavelengths in the spectral response so as to make a baseline determination. The method also includes ascertaining a presence of at least one designated peak within the range of wavelengths as a function of the baseline determination, and evaluating the presence of each of the at least one designated peaks so as to provide an indication of whether the colored gem stone requires further evaluation.

In yet another embodiment of the invention, a computer readable storage medium having computer readable instructions for performing a plurality of functions is provided. Within such embodiment, the functions include receiving a spectral response of a colored gem stone which has been cooled to below a designated temperature and sampling a noise component within a range of wavelengths in the spectral response so as to make a baseline determination. The computer readable storage medium further includes computer readable instructions for performing the function of determining a presence of at least one designated peak within the range of wavelengths as a function of the baseline determination. Within such embodiment, computer readable instructions are also provided for performing the function of outputting an indication of whether the colored gem stone requires further evaluation such that the output is a function of the presence of each of the at least one designated peaks.

It is therefore an object of the present invention to provide a computer based system and method for spectral analysis of gem spectral responses.

It is another object of the present invention to provide a computer based system and method for evaluating a colored gem stone which has been cooled to below a designated temperature.

These and other objectives, features and advantages of the present invention will be more readily understood upon consideration of the accompanying drawings and detailed description.

DETAILED DESCRIPTION OF THE INVENTION

Figure 1:
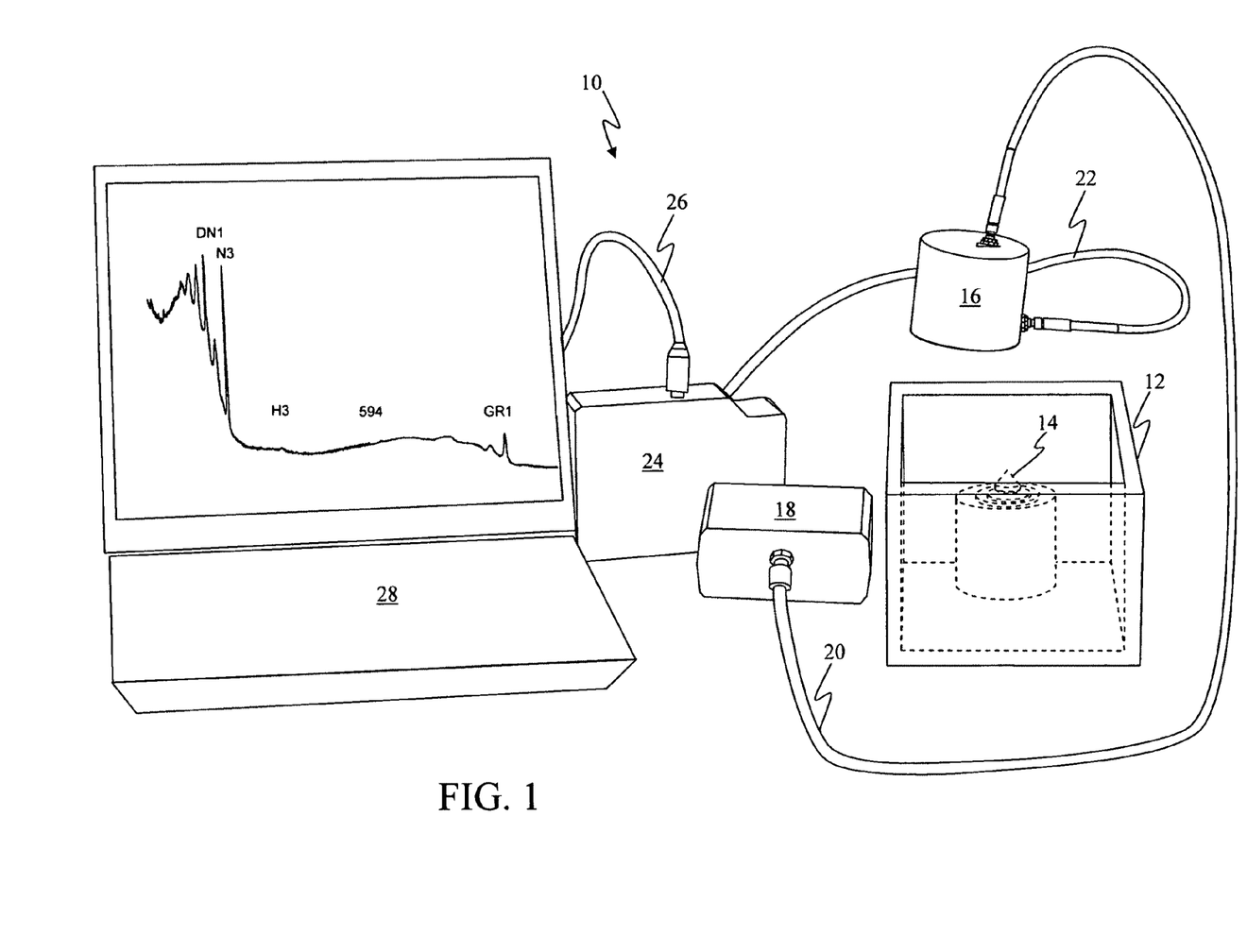
FIG. 1 is a simplified diagram illustrating a system for gem spectral analysis in accordance with an embodiment of the present invention.

Referring to FIG. 1, the components of an embodiment of a gem spectral analysis system 10 in accordance with the present invention will now be described. A gem cooling apparatus 12 is provided for cooling the gem 14 under evaluation to a desired temperature. Gem cooling apparatus 12 may be the apparatus described in U.S. patent application Ser. No. 12/380,416 entitled "METHOD AND APPARATUS FOR RAPIDLY COOLING A GEM", filed even-date herewith, and incorporated by reference herein in its entirety.

An integrating sphere unit 16 is placed over gem 14 that has been cooled in cooling apparatus 12. Integrating sphere unit 16 illuminates the gem 14 with electromagnetic radiation, which may be light of selected wavelengths, and then employs an integrating sphere to gather the spectral response of the illuminated gem. Integrating sphere unit 16 may be implemented using model no. AvaSphere-40, manufactured by Avantes of the Netherlands. The selected wavelengths of light for illuminating gem 14 may be provided by a light source 18, such as a tungsten halogen light source model AVALight-Hal-S, manufactured by Avantes BV of RB Eerbeek, Netherlands. Optical cable 20 may be used to route light from light source 18 to the integrating sphere unit 16. The gathered spectral response from integrating sphere unit 16 may be routed over optical cable 22 to a high resolution spectrometer unit 24, such as model no. HR4000, manufactured by Ocean Optics of Dunedin, Fla. The high resolution spectrometer unit 24 measures the amount of light in the gathered spectral response and transforms the measurements into digital information. The gathered spectral response data, in digital form, is then provided for further processing by computer 28. Cable 26 may be used to couple spectrometer unit 24 to computer 28 to provide a path for the spectral response data.

Computer 28 preferably runs software applications by which the spectral response information from spectrometer unit 24 may be further processed. Such processing may include displaying on a computer screen an image of a depiction of the spectral response as a function of wavelength, as shown in FIG. 1, and/or detecting and analyzing characteristics of the spectral response, and/or extracting specified data from the spectral response information, and the like. Although a laptop computer is depicted in FIG. 1, it is to be understood that other computing or processing devices such as a desktop computer or dedicated controller unit, and the like, may be used, with or without an image display, within the spirit of the present invention.

Instead of the cooling configuration shown in FIG. 1, a two-stage cooling apparatus and spectrometers with higher resolution may be used to provide the spectrum to be analyzed, as described more fully in U.S. patent application Ser. No. 12/380,445, entitled "METHOD AND APPARATUS FOR RAPIDLY COOLING A GEM, INCLUDING TWO STAGE COOLING", filed even-date herewith, and incorporated by reference herein in its entirety.

Figure 2:
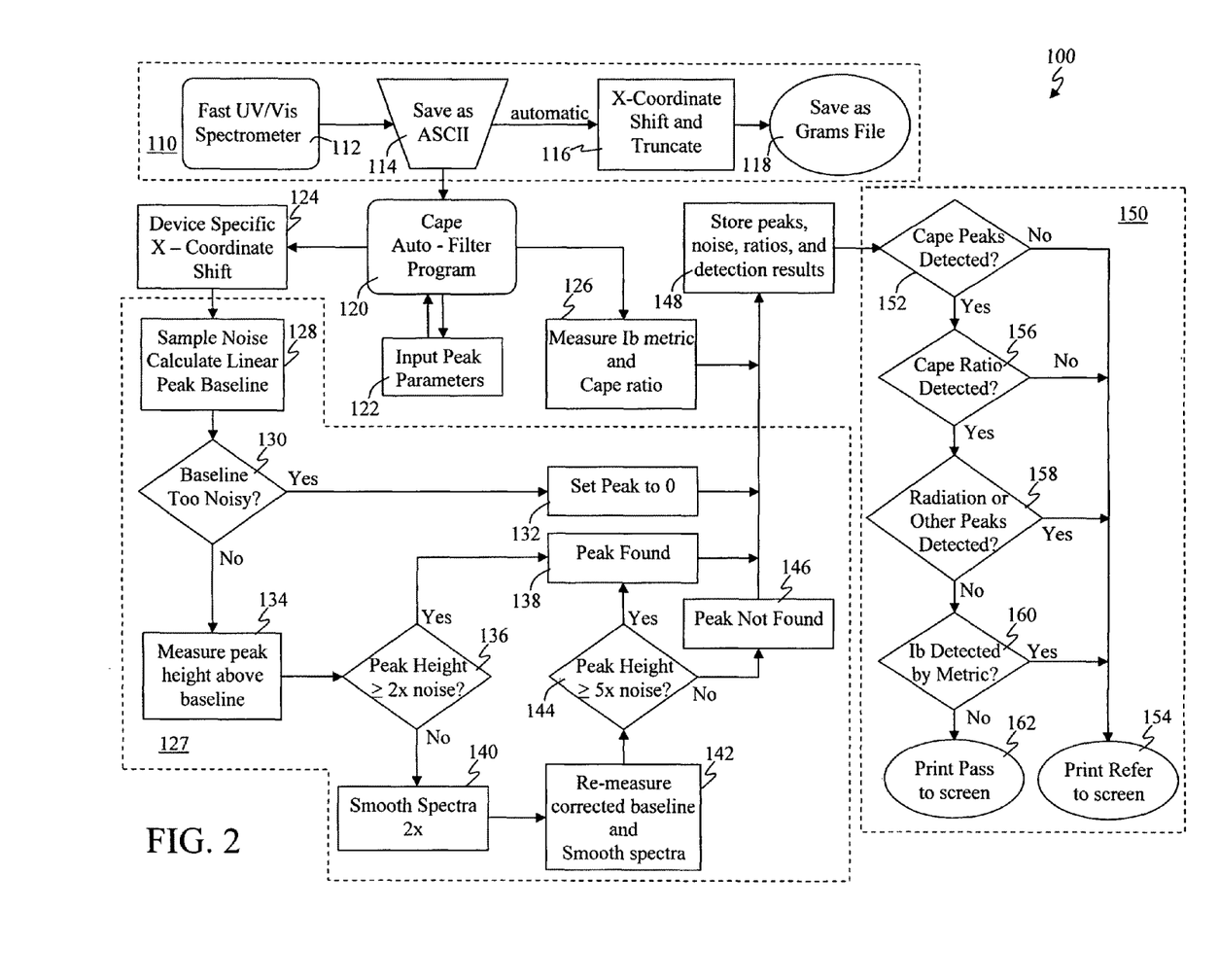
FIG. 2 is a simplified diagram illustrating the acquisition and processing of the spectral response of a gem in accordance with an embodiment of the present invention.

Referring now to FIG. 2, a software application 100 will now be described by which, in accordance with an embodiment of the present invention, the spectral response may be analyzed and indications provided as to whether or not a gem stone, such as a diamond, should be referred for further evaluation as to whether the stone has been subjected to color-altering treatment.

In FIG. 2, the collection of blocks 110 provides preliminary processing of the spectral response data from high resolution spectrometer unit 24, represented by block 112. This includes conversion of the data into ASCII form (block 114), adjusting the data to account for spectrometer device-specific offsets, calibration factors and noise (block 116), and to save the information in an industry standard GRAMS format (in block 118). GRAMS is an acronym for "Graphic Relational Array Management System."

Software implementing the processes of the collection of blocks 110 is commercially available, such as in the Spectra-Suite operating software from Ocean Optics. For example, with spectrometer model no. HR4000, identified above, data such as wavelength calibration and linearity coefficients unique to the spectrometer is programmed into a memory chip embedded in the unit. The SpectraSuite program will read such data from the memory chip and perform appropriate adjustments in the received data using the calibration and linearity coefficients.

In FIG. 2, block 120 is the entry point for a spectral analysis, automatic filter program in accordance with an embodiment of the present invention. Proceeding from block 120 the program may, in block 122, permit the input of parameters indicating what are the peaks and peak characteristics to be evaluated in the received spectral response information; or, beginning with block 124, perform the evaluation of the spectral response according to the peak parameter information entered in block 122; or, in block 126, measure Ib and Cape Ratio information in the received spectral response information; or perform combinations of some or all of the foregoing.

With respect to the input of parameters indicating what are the peaks and peak characteristics desired to be evaluated in the received spectral response information, in block 122, examples of such parameters are discussed below in connection with FIG. 3.

In connection with the evaluation of spectral response that begins at block 124, the ASCII form of the spectral response information is received from block 114, and then x-coordinate shifted and truncated in a manner similar to that in block 116. This provides a calibration of the data which is specific to the spectrometer that was used to acquire the data, and provides truncation of the data, as appropriate, to reduce noise. Preferably, truncation is used because typically, only certain regions of the electromagnetic spectrum are optimal for the array of sensors used in the hardware. If data is collected beyond this range, the spectral signature is quite noisy and often useless. We prefer to truncate those noisy regions, which allows a spectrum to be normalized more appropriately for display. Preferably, data are truncated to an upper limit of 1000 nm since spectrum above 1000 nm is usually quite noisy. Truncation to an upper limit will not reduce noise in other regions.

Following the x-coordinate shift and truncation operation in block 124, peak detection operations are conducted by the collection of blocks 127. In block 128, the noise in the spectral response data is sampled, and, if possible, a linear peak baseline is determined. FIG. 3 illustrates, in accordance with an embodiment of the present invention, an embodiment of the linear baseline determination operation of block 128. The plotted portion of FIG. 3 illustrates an example of received spectral information, a graphical depiction of the values determined in connection with the baseline determination, and a particular baseline that was determined in association with a particular peak in the received spectral information. The lower portion of FIG. 3 is a listing of the parameters used in the evaluation of the spectral information. In accordance with an embodiment of the invention, such parameters may be provided by way of block 122, FIG. 2, about the peak or peaks desired to be detected in the particular example. It is to be understood that any number of peaks identifiers and measurement criteria may be programmed into the system by a programmer by way of block 122. Preferably, the peak parameters cannot be changed by a user of the system. Preferably, these peak parameters have been optimized so that the same stones would be passed/referred in a manner similar to a review manually by experienced staff. The system may also have selected peak designations and corresponding measurement criteria which have been pre-programmed, or preset, or selectable in connection with default operations of the analysis system and method.

Figure 3:
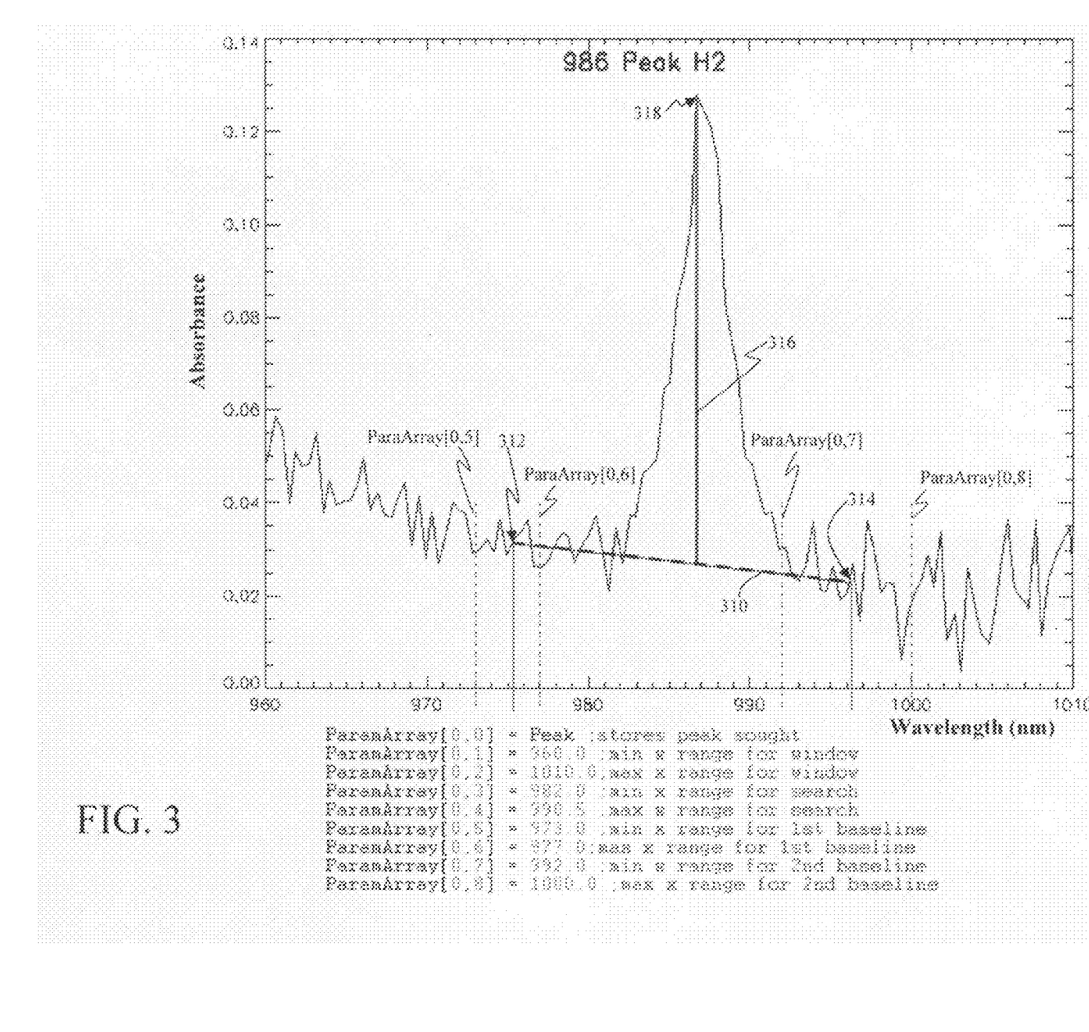
FIG. 3 is a simplified diagram illustrating the determination of a linear peak baseline and measurement of peak height in an acquired spectral response in accordance with an embodiment of the present invention.

As can be seen from the lower portion of the example of FIG. 3, the parameters may take the form of a two dimensional array, of nine (9) fields of information that are designated for use in the analysis of the particular example. The array has the form of ParamArray[x,y], where "x" serves as a peak identifier, and "y" corresponds to a particular parameter associated with peak "x". In this example, a comments field is provided for each parameter in the list, and is indicated by and to the right of the semi-colon symbol, ";". The comments field provides a brief description of the purpose of the corresponding parameter.

ParamArray[0,0] is used to provide the identity of the peak being searched for, and typically is a wavelength that is the approximate location of where the peak is usually found. In this example, the H2 peak at 986 nm, is the peak of interest.

ParamArray[0,1] and ParamArray[0,2] specify the end-point wavelengths of a window which brackets the portion of the received spectral information to be evaluated for the peak specified by ParamArray[0,0]. For the example of FIG. 3, the window extends from 960.0 nm to 1010.0 nm.

ParamArray[0,3] and ParamArray[0,4] identify the range of wavelengths to be searched within the designated window in the received spectral information for the peak identified by ParamArray[0,0]. For the example of FIG. 3, the range extends from 982.0 nm to 990.0 nm.

In a preferred embodiment of the present invention, the baseline determination operation of block 128 determines two baseline values, one in a first range of wavelengths below the wavelength of the peak identified by ParamArray[0,0], the second in a second range of wavelengths above wavelength of the peak identified by ParamArray[0,0]. In the example of FIG. 3, ParamArray[0,5] and ParamArray[0,6] indicate the end points of the first range of wavelengths, while ParamArray[0,7] and ParamArray[0,8] indicate the end points of the second range of wavelengths. For the example of FIG. 3, the first range extends from 973.0 nm to 977.0 nm, while the second range extends from 992 nm to 1000.0 nm. It is to be noted that the first wavelength range and second wavelength range correspond to areas of the received spectral response to either side of the identified peak, and which areas are not expected to contain peaks other than noise peaks.

In order to determine the first baseline value, corresponding to the first range of wavelengths below the wavelength of the peak identified by ParamArray[0,0], the average of all the x values and the average of all the y values for the range of 973 nm to 977 nm is taken. For the example of FIG. 3, the average x value is about 975 nm, and the average y value is about 0.0315. There can be slight shifts in the calculation and the plotting depending on how closely the end point x coordinates are to the range specified and how accurately the endpoints of the baseline are displayed and discerned on the plot. These average values are then assigned as the first baseline values. In the example of FIG. 3, the first baseline value can be seen to be about 0.0315 at a wavelength of about 975.4 nm.

The second baseline value, corresponding to the second range of wavelengths above the wavelength of the peak identified by ParamArray[0,0], is determined in a manner similar to that used in determining the first baseline value. In the example of FIG. 3, the second baseline value can be seen to be about 0.0233 at a wavelength of about 996.2 nm.

A baseline slope is then calculated using the first and second baseline values. In FIG. 3, dashed line 310 is shown which graphically illustrates the determined baseline for the example. The baseline 310 extends between the first baseline value 312 and the second baseline value 314, and is inclined at the baseline slope. Baseline information is determined in a similar matter for other designated peaks, as specified, for example, by information input into the system in block 122, FIG. 2. The foregoing baseline information is then used in subsequent peak detection and other operations upon the received spectral response information.

In a preferred embodiment, to determine the noise value, the mean and standard deviation are calculated of the Y values. The estimate of noise is then the standard deviation of $Y*2$. A noise value is determined in this manner for baseline 1 and another from baseline 2. Preferably, the highest of these values is used to compare with the peak height in a later phase of the data analysis.

In block 130 of FIG. 2, if the noise sample indicates that the data is too noisy for peak detection, the value for the peak is set to "0" in block 132. In a preferred embodiment of the invention, a "too noisy" condition is indicated if the noise samples exceed a specified maximum noise threshold. For example a maximum noise level of 0.03 may be used for H2 in the example of FIG. 3. Such maximum noise threshold can be viewed as a static noise threshold. It is to be understood that such specified thresholds may differ depending upon the part of the spectrum being analyzed. For example, it has been observed that noise levels can be higher around H2 peaks, therefore a higher maximum noise threshold may be specified when attempting to measure H2 peaks in received spectral response information.

In block 130, if, on the other hand, the sampled noise level is below the noise threshold, a measurement is made in block 134 of the level of the specified peak above the baseline. Returning to FIG. 3, an example is provided of the measurement of an H2 peak, in accordance with an embodiment of the present invention. Recall that ParamArray[0,3]=982.0 nm and ParamArray[0,4]=990.5 nm, as input by way of block 122, specify the range of wavelengths to be searched for an H2 peak in the received spectral response information. The specified search range is searched for a maximum level in the spectral information (the peak value) within the search range, and the wavelength at which the maximum (peak value) is found.

If a peak value is found, its corresponding wavelength is applied to the baseline information that had been determined earlier in block 128, FIG. 2, in order to determine the value of the baseline at the wavelength at which the peak value occurs. The amount by which the peak value exceeds the determined value of the baseline at the peak value wavelength is then determined and examined in block 136, FIG. 2. This amount is graphically illustrated in FIG. 3 by the solid vertical line 316 that extends from baseline 310 to peak 318 of the plot.

If, in block 136, FIG. 2, it is determined that the amount by which the height of the peak exceeds the baseline value is greater than or equal to two (2) times the noise value, an indication is set in block 138 that a peak has been found. Block 136 can be viewed as comparing the height of the peak to a relative noise threshold. On the other hand, if the height of the peak does not exceed the baseline value by at least two (2) times the noise value, a further processing and re-measurement of the spectral response information is performed in blocks 140, 142 and 144. In block 140, the spectral response information is operated upon by a smoothing filter, preferably a 2× smoothing filter. Such smoothing filters are well know, such as those available as a part of the well known Interactive Data Language ("IDL") programming language. The smoothed spectral information is then baseline corrected (sloped baseline and corresponding spectral region are corrected trigonometrically to become horizontal) and then re-measured in block 142 to determine noise and peak height information. Then, in block 144, the peak height is checked to determine if the amount by which the height of the peak exceeds the noise value is greater than or equal to five (5) times the noise value. A larger relative noise threshold is used for evaluating the smoothed spectral response information in order to reduce the chances of random noise being mistaken for a peak. This larger relative noise threshold can be viewed as a designated smoothed spectrum noise threshold.

If, in block 144, it is determined that the amount by which the height of the peak exceeds the noise value is greater than or equal to five (5) times the noise value, an indication is set in block 138 that a peak has been found. On the other hand, if the height of the peak does not exceed the noise value by at least five (5) times the noise value, a peak not found indication is set in block 146. The results of the peak detection operations of the collection of blocks 127 are stored by way of block 148, FIG. 2.

Among the other operations performed in an embodiment of the present invention are the measurement of an Ib metric and a determination of Cape Ratios, as indicated for block 126 of FIG. 2. Preferably, the peak detection techniques, or similar, discussed in connection with collection of blocks 127 are used in these Cape Ratios and Ib metric measurements, as well as in the examination of the spectral response for the presence of Cape Peaks.

In a preferred embodiment, in order for a Cape Ratio to be deemed present, a negative slope to a certain degree must be present (as indicated by the cape ratio) and one or more peaks of designated wavelengths must be present.

A preferred metric for determining whether the spectral response includes data indicative of a Cape stone involves examination of the data for the presence of a cape ratio as follows. First, the average of the Y (magnitude) values over a first range of wavelengths is determined, for example over 600 to 610 nm. Next, the average of the Y (magnitude) values over a second range of wavelengths, below the first range, is determined, for example, over 430 to 440 nm. The difference between the averaged values is then determined, and then divided by the difference between the mid-points of the first and second ranges. For example, the difference between mid-points 605 nm and 435 nm would be 170 nm. For the particular example being discussed, the equation for the cape ratio would be:

$$\text{Cape Ratio (slope)} = \{[\text{average } Y \text{ value } (600-610)] - [\text{average } Y \text{ value } (430-440)]\} / [\text{Average } X(605-435)]$$

If the slope is determined to be negative enough, the stone is identified as a cape diamond. If slope is positive, or not steep enough, then the stone is referred for further evaluation. As an example, a slope which is not steep enough may have a value which is greater than minus 0.0002. Thus, for this example, a slope of minus 0.0001 would be considered not negative enough.

Figure 4:
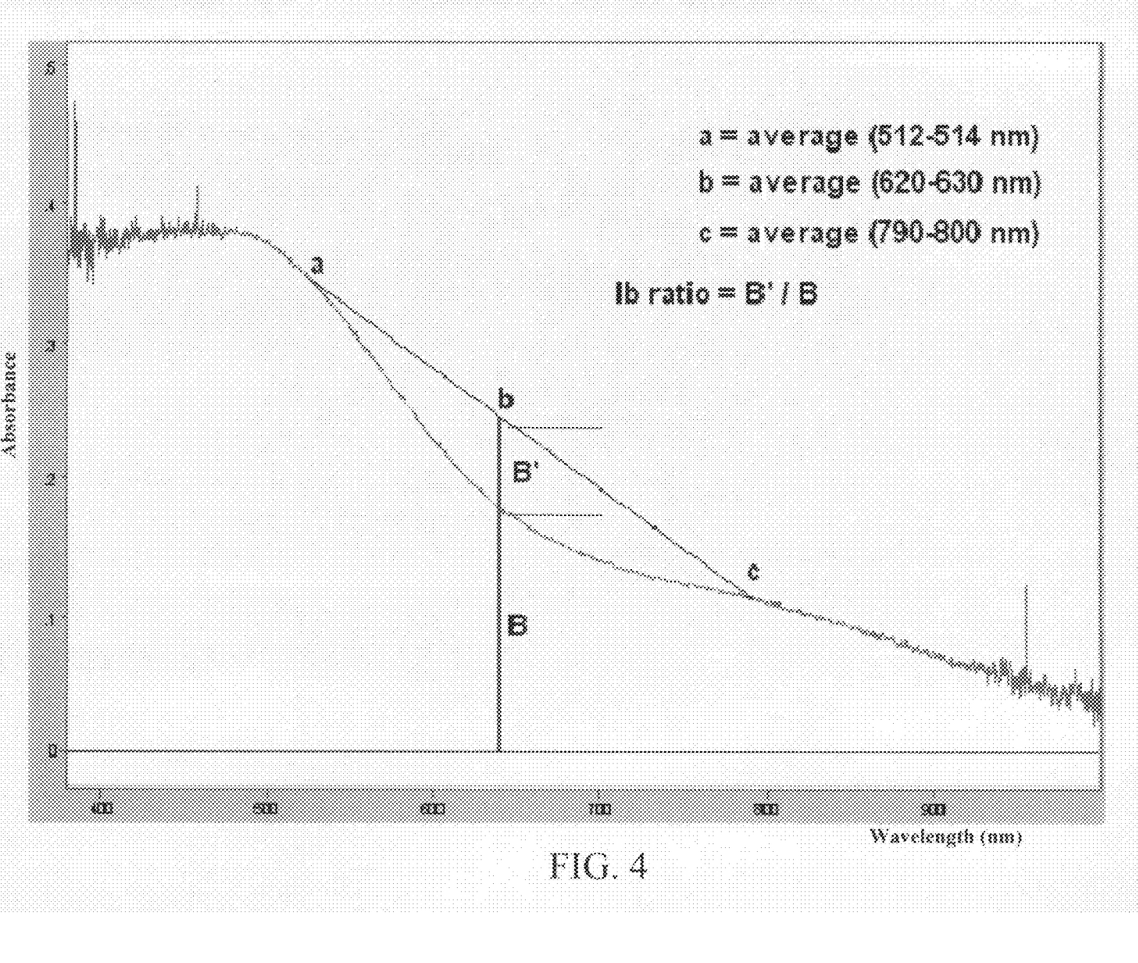
FIG. 4 is a simplified illustration of the operations performed on an acquired spectral response by an absorption related to isolated nitrogen in diamond metric for detecting a possible 1b gem in accordance with an embodiment of the present invention.

FIG. 4 provides an illustration of a absorption related to isolated nitrogen in diamond metric for detection of "Ib" stones, in accordance with an embodiment of the invention. This metric is directed to capturing the curvature in the spectrum around a specified wavelength, such as 600 nm or 640 nm. In this embodiment, a linear function is defined between two points (e.g. points "a" and "c") in the received spectrum. At a designated wavelength between the two points, a ratio is determined between a first quantity and a second quantity. The first quantity is the difference (indicated by B') between the value of the linear function at the designated wavelength (indicated by b) and the actual value of the spectral response at the designated wavelength (indicated by B). The second quantity is the actual value of the spectral response at the designated wavelength (indicated by B). If the magnitude of the determined ratio does not exceed a specified threshold, the stone is referred for further evaluation. For the example provided in FIG. 4, a specified threshold for the Ib ratio may be 0.6.

The two points used for determining the above linear function for the lb metric may be identified, for example, by determining the average value of the spectral response in specified ranges of wavelengths, much like the approach used in determining baseline information in block 128, as described herein above. In the example of FIG. 4, the first point, "a," is identified by determining the average value of the spectral response in the 512 to 514 nm range of wavelengths. The second point, "c," is determined in accordance with the example by taking the average value of the spectral response in the 790 to 800 nm range of wavelengths.

In accordance with the lb metric example in FIG. 4, the designated wavelength at which the ratio is taken may be determined by taking the average of the spectral response over a range of wavelengths between the ranges used for first point "a" and second point "c." Such a range may be, for example, 620 to 630 nm, with point "b" being the point corresponding to the average value determined for the range. The corresponding wavelength for the determined value of average spectral response is then identified and applied to the linear function to determine the value, B, of the linear function at that wavelength. The difference, B', between the linear function value and the average value, B, is then determined. Then, the ratio B'/B is evaluated to determine whether it exceeds a designated threshold. Depending upon the results of such evaluation, the stone may be referred for further evaluation or passed.

In other embodiments of the invention, the lb metric may take the form of determining the second (2nd) derivative of the spectral response about a designated wavelength in a range of wavelengths. For example, the second derivative of the spectral response about 640 nm in the 512 to 800 nm range may be determined as a part of the lb metric.

Other possible forms of the lb metric can involve calculating the difference between 2 or more slopes and comparing those differences to the differences calculated from a reference spectrum or determined empirically from a series of reference spectra.

Returning now to FIG. 2, once the lb metric and the Cape ratio for the stone are measured in block 126, the results of such measurements are stored, see block 148.

The measurements and data stored by way of block 148 are evaluated in the collection of blocks 150, in order to provide a "Pass" or "Refer" designation for the stone being evaluated. An illustrative example of such an evaluation is provided in FIG. 2. In blocks 152 and 156 the information is examined to determine whether Cape Peaks were detected and whether the Cape Ratio is consistent with a cape diamond. If all cape peaks were not found or Cape Ratio was not indicative of cape, a "Refer" designation will be generated for the stone. Such designation may be supplied by way of a "print Refer to screen" operation of block 154, in which a "Refer" indication is displayed on a visual display to the operator. Those skilled in the art will recognized that other forms may be used by which a "Refer" designation is indicated, such as by an audible signal, activation of an indicator light, or entry of a "Refer" value into a field of a data base record for the stone, and the like.

In collection of blocks 150 of FIG. 2, if Cape Peaks were not all detected in block 152, or Cape Ratio was not consistent with cape diamond in block 156, or radiation peaks were detected in block 158, or lb ratio in block 160 indicated that lb nitrogen was present then for the stone, a "Refer" designation will be generated for the stone, as above, see block 154. The measurement and peak detection results are examined in block 158 for the presence of radiation or other specified peaks, such as one that is indicative of an artificial pink coating of diamonds is also checked.

Conversely, if Cape Peaks were detected in block 152, and a Cape Ratio was detected in block 156, and Radiation or Other Peaks were not detected in block 158, and no lb was indicated in block 160, a "Pass" designation will be generated for the stone. As above, for a "refer" designation, a "Pass" designation may be supplied by way of a "print Pass to screen" operation of block 162, in which a "Pass" indication is displayed on a visual display to the operator. Those skilled in the art will recognized that other forms may be used by which a "Pass" designation is indicated, such as by an audible signal, activation of an indicator light, or entry of a "Pass" value into a field of a data base record for the stone, and the like.

It is to be understood that although a particular sequence of steps has been described above in connection with the "refer" or "pass" evaluation, there is no intention to limit the scope of the invention solely to such sequence, and that such steps may be undertaken in a variety of different sequences within the spirit of the invention.

The terms and expressions which have been used herein are terms of description and not of limitation, and there is no intention in the use of such terms of excluding equivalents of the features shown and described, or portions thereof, it being recognized that various modifications are possible within the scope of the invention claimed.

The invention claimed is:

1. A method for evaluating a colored gem stone which has been cooled to below a designated temperature, comprising
    generating a spectral response of the colored gem stone over ranges of wavelengths of electromagnetic radiation;
    evaluating the spectral response for the presence of a plurality of designated peaks, including
        determining from the spectral response a corresponding linear peak baseline for peaks of the plurality of designated peaks and an associated noise value for the linear peak baseline;
        determining for each of the plurality of designated peaks, a height of the designated peak above the corresponding linear peak baseline; and
        indicating that a designated peak has been found when the associated noise value and the determined height of the designated peak above the corresponding linear peak baseline satisfy designated noise thresholds; and
    generating a pass indication or a refer indication as a function of a combination of the evaluation results for the presence of the plurality of designated peaks.

2. The method of claim 1, wherein the designated noise thresholds include a static noise threshold and a relative noise threshold.

3. The method of claim 2, wherein the relative noise threshold is a multiple of the static noise threshold.

4. A method for evaluating a colored gem stone which has been cooled to below a designated temperature, comprising
    generating a spectral response of the colored gem stone over a range of wavelengths of electromagnetic radiation;
    evaluating the spectral response with an lb metric for the presence of an lb characteristic;
    evaluating the spectral response for the presence of a Cape Ratio;
    evaluating the spectral response for the presence of a plurality of designated peaks including a radiation peak and cape peaks; and generating a pass indication or a refer indication as a function of results of the Ib metric evaluation, results of the radiation and cape peaks evaluation, and results of the Cape Ratio evaluation.

5. The method of claim 4, wherein a pass indication is generated when a cape peak is detected, a radiation peak is not detected, a cape ratio is detected, and an Ib is not detected; and a refer indication is generated when cape peaks are not detected, or a radiation peak is detected, or a cape ratio is not detected, or an Ib is detected.

6. The method of claim 4, wherein the step of evaluating the spectral response for the presence of a plurality of designated peaks, includes the steps of
   determining from the spectral response a corresponding linear peak baseline for peaks of the plurality of designated peaks and an associated noise value for the linear peak baseline;
   determining for each of the plurality of designated peaks, a height of the designated peak above the corresponding linear peak baseline; and
   indicating that a designated peak has been found when the associated noise value and the determined height of the designated peak above the corresponding linear peak baseline satisfy designated thresholds.

7. The method of claim 6, wherein the step of determining a linear peak baseline includes the steps of
   averaging the spectral response for a range of wavelengths below a designated peak wavelength;
   averaging the spectral response for a range of wavelengths above the designated peak wavelength; and
   defining the linear peak baseline corresponding to the designated peak wavelength based upon the averaged spectral responses.

8. The method of claim 6, further including
   smoothing the received spectral response by 2× using a smoothing filter and baseline correction when the determined height of the designated peak above the linear peak baseline is less than the designated noise threshold;
   determining a corrected baseline from the smoothed spectral response;
   determining for the designated peak, a height of the designated peak in the smoothed spectral response above the corrected baseline; and
   indicating that the designated peak has been found when the determined height of the designated peak above the corrected baseline equals or exceeds a designated smoothed spectrum noise threshold which is greater than the designated threshold.

9. The method of claim 8 wherein the step of determining a corrected baseline includes the steps of
   averaging the smoothed spectral response for a range of wavelengths below a designated peak wavelength;
   averaging the smoothed spectral response for a range of wavelengths above the designated peak wavelength; and
   defining the corrected baseline corresponding to the designated peak wavelength from the averaged smoothed spectral responses, including trigonometric correction of the averaged smooth spectral responses and corresponding spectral region to provide a horizontal baseline.

10. The method of claim 4 wherein the metric for the presence of an Ib characteristic comprises the steps of
    determining a first average of the spectral response over a first range of wavelengths;
    determining a second average of the spectral response over a second range of wavelengths above the first range of wavelengths;
    determining a third average of the spectral response over a third range of wavelengths between the first and the second ranges of wavelengths, and a corresponding wavelength in the third range of wavelengths at which the third average is found in the spectral response;
    constructing a linear function based upon the first average and the second average;
    applying the determined corresponding wavelength to the linear function to determine a corresponding linear function value;
    determining a ratio between a first quantity, determined by the difference between the linear function value and the third average, and a second quantity, determined by the third average; and
    comparing the determined ratio to a designated Ib threshold.

11. The method of claim 4 wherein the metric for the presence of an Ib characteristic comprises
    determining a second derivative of the spectral response data about a designated wavelength or wavelengths; and
    comparing the determined second derivative to a designated threshold.

12. The method of claim 4 wherein the metric for the presence of an Ib characteristic comprises the steps of
    comparing differences in slopes of the spectral response data at a plurality of designated wavelengths; and
    determining whether the differences in slopes meets a designated threshold.

13. The method of claim 4 wherein the presence of a Cape Ratio is determined by determining whether a plateau is present in the spectral response in a selected range of wavelengths, and determining whether a peak is present at a designated wavelength in the selected range of wavelengths.

14. A system for processing spectral information from a gem stone, comprising:
    a cooling unit configured to support and cool a gem stone to below a desired temperature;
    an electromagnetic radiation source;
    a spectrometer;
    an integrating sphere coupled to the electromagnetic radiation source and to the spectrometer, and positionable in the cooling unit to provide to the spectrometer responsive electromagnetic spectrum collected from a gem stone supported in the cooling unit and which has been illuminated with electromagnetic radiation from the electromagnetic radiation source;
    a processing unit configured to analyze spectral response information received from the spectrometer, the analysis including:
      evaluating the spectral response with an Ib metric for the presence of an Ib characteristic;
      evaluating the spectral response for the presence of a Cape Ratio;
      evaluating the spectral response for the presence of a plurality of designated peaks including a radiation peak and cape peaks;
      generating a pass indication or a refer indication as a function of results of the Ib metric evaluation, results of the radiation and cape peaks evaluation, and results of the Cape Ratio evaluation.

15. A method for evaluating a colored gem stone which has been cooled to below a designated temperature, comprising
    generating a spectral response of the colored gem stone;
    sampling a noise component within a range of wavelengths in the spectral response so as to make a baseline determination;

ascertaining a presence of at least one designated peak within the range of wavelengths as a function of the baseline determination; and evaluating the presence of each of the at least one designated peaks in connection with the baseline determination so as to provide an indication of whether the colored gem stone requires further evaluation.

16. The method of claim 15, wherein the at least one designated peak includes a cape peak.

17. The method of claim 15 further comprising the step of evaluating the spectral response for the presence of a Cape Ratio so as to provide another indication of whether the colored gem stone requires further evaluation.

18. The method of claim 17, wherein the presence of a Cape Ratio is determined by determining whether a plateau is present in the spectral response in a selected range of wavelengths, and determining whether a peak is present at a designated wavelength in the selected range of wavelengths.

19. The method of claim 15 further comprising the step of evaluating the spectral response with an lb metric for the presence of an lb characteristic so as to provide another indication of whether the colored gem stone requires further evaluation.

20. The method of claim 19, wherein obtaining the metric for the presence of an lb characteristic comprises the steps of
comparing differences in slopes of the spectral response data at a plurality of designated wavelengths; and
determining whether the differences in slopes meet a designated threshold.

21. A tangible non-transitory computer readable storage medium having computer readable instructions for performing the functions of:
generating a spectral response of a colored gem stone which has been cooled to below a designated temperature;
sampling a noise component within a range of wavelengths in the spectral response so as to make a baseline determination;
determining a presence of at least one designated peak within the range of wavelengths as a function of the baseline determination; and
outputting an indication of whether the colored gem stone requires further evaluation, wherein the output is a function of the presence of each of the at least one designated peaks.

22. The computer readable storage medium of claim 21, wherein the instructions for determining the presence of at least one designated peak include instructions for performing the functions of:
determining from the spectral response a corresponding linear peak baseline;
determining for each of the at least one designated peaks, a height of the designated peak above the corresponding linear peak baseline; and
indicating that a designated peak has been found when the determined height of the designated peak above the corresponding linear peak baseline equals or exceeds a first designated threshold.

23. The computer readable storage medium of claim 22, wherein the instructions for determining a linear peak baseline include instructions for performing the functions of:
averaging the spectral response for a range of wavelengths below a designated peak wavelength;
averaging the spectral response for a range of wavelengths above the designated peak wavelength; and
defining the linear peak baseline corresponding to the designated peak wavelength based upon the averaged spectral responses.

24. The computer readable storage medium of claim 22 further including instructions for performing the functions of
smoothing the received spectral response by 2× using a smoothing filter when the determined height of the designated peak above the linear peak baseline is less than the designated threshold;
determining a corrected baseline from the smoothed spectral response;
determining for the designated peak, a height of the designated peak in the smoothed spectral response above the corrected baseline; and
indicating that the designated peak has been found when the determined height of the designated peak above the corrected baseline equals or exceeds a second designated threshold which is greater than the first designated threshold.

25. The computer readable storage medium of claim 21, wherein the at least one designated peak includes a cape peak.

26. The computer readable storage medium of claim 21 further comprising instructions for evaluating the spectral response with an lb metric for the presence of an lb characteristic, wherein the output is a function of the presence of the lb characteristic.

27. The computer readable storage medium of claim 21 further comprising instructions for evaluating the spectral response for the presence of a Cape Ratio, wherein the output is a function of the presence of the Cape Ratio.

* * * * *